United States Patent [19]
Collin et al.

[11] Patent Number: 5,959,137
[45] Date of Patent: Sep. 28, 1999

[54] PRIMARY AMINE SALTS DERIVED FROM AMINO ACIDS CONTAINING A URETHANE GROUP, AND THEIR USE IN COSMETIC COMPOSITIONS

[75] Inventors: Nathalie Collin, Sceaux; Didier Candau, Bievres; Eric Quemin, Villepinte, all of France

[73] Assignee: L'Oreal, Paris, France

[21] Appl. No.: 08/290,748

[22] PCT Filed: Dec. 16, 1993

[86] PCT No.: PCT/FR93/01255

§ 371 Date: Nov. 1, 1994

§ 102(e) Date: Nov. 1, 1994

[87] PCT Pub. No.: WO94/13628

PCT Pub. Date: Jun. 23, 1994

[30] Foreign Application Priority Data

Dec. 16, 1992 [FR] France ................................. 92 15162

[51] Int. Cl.[6] ................................................. C07C 261/00
[52] U.S. Cl. .............................. 560/160; 514/47; 514/59; 514/63; 514/70.22
[58] Field of Search ............................. 560/160; 514/47, 514/59, 63, 70.22

[56] References Cited

U.S. PATENT DOCUMENTS

| | | | |
|---|---|---|---|
| 4,282,203 | 8/1981 | Jacquet | 424/47 |
| 4,324,780 | 4/1982 | Jascquet | 424/47 |
| 4,595,585 | 6/1986 | Papantoniou | 424/47 |
| 5,112,601 | 5/1992 | Sebag | 560/160 |
| 5,182,407 | 1/1993 | Sebag | 554/52 |
| 5,230,890 | 7/1993 | Philippe | 424/401 |
| 5,470,579 | 11/1995 | Bonte | 424/450 |

FOREIGN PATENT DOCUMENTS

| | | |
|---|---|---|
| 0408448 | 1/1991 | European Pat. Off. . |
| 0468856 | 1/1992 | European Pat. Off. . |
| 2649697 | 1/1991 | France . |
| 2604625 | 4/1998 | France . |

OTHER PUBLICATIONS

Michalun, "Milday's Skin Care and Cosmetic Ingredients Dictionary," pp. 76 & 294 May, 1994.

*Primary Examiner*—Michael L. Shippen
*Attorney, Agent, or Firm*—Nixon & Vanderhye, P.C.

[57] ABSTRACT

Primary amine salts of derivatives having formula: R'O—CO—NH—CH(R)—COOH wherein R is —$CH_2OH$ or —CHOHO—$CH_3$, and R' is an optionally insaturated alkyl group having at least 10 carbon atoms, as well as the least partial salification products of the derivatives of formula (I) with primary amines, and whose salification degree is sufficient to obtain, in aqueous solution, a pH higher than 6 and lower than 7.5; and cosmetic compositions, in the form of emulsions, containing them. These primary amine salts which have hydrating properties for the skin, have also the property of stabilizing emulsions.

25 Claims, No Drawings

PRIMARY AMINE SALTS DERIVED FROM AMINO ACIDS CONTAINING A URETHANE GROUP, AND THEIR USE IN COSMETIC COMPOSITIONS

The invention relates to new primary amine salts of urethanes derived from amino acids, and to their use, in particular, as emulsifying and hydrating agents in cosmetic compositions.

In Patent Application FR 89/09328 (Publication No. 2,649,697), urethanes derived from certain amino acids or from the salts of the said acids have been described as hydrating agents or surfactants in cosmetic or pharmaceutical compositions intended for the treatment of dry skins. In this prior patent application, the preparation of certain salts is described, in particular metal salts, ammonium salts and tertiary amine salts.

However, the use of the urethane derivatives and of their salts described in the prior patent application creates particular formulation problems. These products, in acid form, are very sparingly soluble in water at room temperature. On heating, for example to approximately 80° C., the formation of a substantially homogeneous gel is achieved. However, the acid pH of such a gel does not permit these products to be formulated in compositions for the skin. In addition, on cooling to room temperature, the acid reprecipitates.

When an attempt is made to circumvent this difficulty by salifying using a base such as sodium hydroxide or triethanolamine, the aqueous phase containing the acid has to be heated. When the gel is formed, an aqueous solution of the chosen base is added dropwise, and when stoichiometry is reached, a clear solution of the salt formed is obtained. However, on cooling to room temperature, the formation of a precipitate is observed, during the cooling or after a few days at most.

An effort has thus been made to solubilize the said urethane derivatives, in a mixture of water and oil, by forming an emulsion in the heated state.

With the unsalified derivatives, microscopic observation shows that a very fine emulsion is obtained at 80° C. However, on cooling to room temperature, the texture becomes completely heterogeneous with, in particular, a precipitation of crystals.

The salts of the said urethane derivatives also enable fine emulsions to be obtained. However, with the tertiary amine salts such as the triethanolamine salt, the emulsion separates into two phases after approximately two weeks.

It has, on the other hand, been discovered that, surprisingly, with some of the said urethane derivatives of serine or threonine, salified with a primary amine, it is possible to obtain emulsions that remain stable for several months.

The subject of the invention is hence the primary amine salts of the derivatives of formula (I):

R'O—CO—NH—CH(R)—COOH            (I)

in which:
R represents —CH$_2$OH or —CHOH—CH$_3$, and R' represents an optionally unsaturated alkyl group having at least 10 carbon atoms, as well as the at least partial salification products of the derivatives of formula (I) with primary amines, and the degree of salification of which is sufficient to obtain a pH above 6 and below 7.5 in aqueous solution.

Salification products are understood here to mean the compounds obtained by salification of the compounds of formula (I) with a primary amine in proportions which are not necessarily stoichiometric. However, in the present application, the expression "primary amine salts" will denote, except where otherwise stated, both the actual salts and the other salification products, and vice versa.

In particular embodiments, the primary amine salts of the derivatives of formula I which are useable according to the invention can possess the following features, taken separately or, where appropriate, in combination:

R' contains from 10 to 20 carbon atoms, and especially from 14 to 18 carbon atoms, and in particular 16 carbon atoms;

the said primary amines correspond to the formula (II):

H$_2$N—CR$_1$(R$_2$) (R$_3$)            (II)

in which:
R$_1$ represents —CH$_2$OH, and R$_2$ and R$_3$ independently represent an optionally hydroxylated lower alkyl; R$_2$ represents, for example, —CH$_3$ or —CH$_2$OH, and R$_3$ can represent —CH$_3$, —C$_2$H$_5$ or —CH$_2$OH;

the primary amine (II) is chosen from 2-amino-2-methyl-1,3-propanediol, 2-amino-2-methyl-1-propanol and 2-amino-2-hydroxymethyl-1,3-propanediol;

or alternatively the primary amine used for the salification of the derivatives of formula I can itself be an amino acid containing at least two amino groups, such as, for example, lysine or arginine.

The process for preparing the compounds of formula I and their salts is described in French Patent Application 89/09328 (Publication No. 2,649,697). It will be recalled that this process is characterized in that a salt of an amino acid (D-, L- or DL-) chosen from serine and threonine is reactive with a compound of formula (III):

X—CO—OR'            (III)

X representing a halogen or a 1-imidazolyl group, in a suitable solvent, in that the corresponding urethane derivative of formula I formed is isolated according to known methods and in that the said urethane derivative is converted according to known methods to a corresponding salt.

The starting salt is, for example, an alkali metal salt or a salt of an amine such as triethylamine.

The reaction between the amino acid salt and the haloformate (preferably chloroformate) may be performed at room temperature in a conventional solvent such as a water/tetrahydrofuran, water/dioxane or water/pyridine mixture.

The reaction between the amino acid salt and the imidazole derivative of formula III may be performed, for example, in N,N-dimethylformamide or N,N-dimethylacetamide at a temperature of 20 to 100° C., for example at 60° C., in the presence of a basic catalyst such as potassium t-butanolate or sodium imidazolide.

Primary amine salts or salification products of the compounds of formula I have advantageous cosmetic properties, in particular skin hydrating properties. They also have surfactant properties which enable them to be used as emulsifying agents. In addition, they have bactericidal properties.

The salts or salification products of the invention may be used as skin hydrating agents in humans. They enable the skin's suppleness, its elasticity, its resistance to body movements and its function as a barrier to the entry of toxic substances to be retained or restored. Cosmetic or dermopharmaceutical compositions intended for hydrating the skin are known to be used, in particular, in people having a so-called dry skin. This phenomenon is characterized by a skin having a markedly higher evaporation rate than that of a healthy skin, by a loss of cutaneous elasticity and by the formation of wrinkles. It may be caused, in particular, by pathological disorders of keratinization, by ageing or by excessive exposure to sunlight or to various external agents (detergents, soaps, solvents, dry atmosphere, and the like). This phenomenon can affect all parts of the body, and especially the face, neck and hands.

The properties of the salts of the invention, in particular when they are applied in compositions in emulsion form, may be demonstrated by different tests. Thus, the favourable influence on skin elasticity may be shown using the apparatus described in the paper by L. Rasseneur et al., Int. J. of Cosm. Sci. 4, 247–260, (1982).

The properties of the salification products of the derivatives of formula I have also been demonstrated using an evaporimeter (Servomed), which is an apparatus which permits quantitative determination of the evaporation of water from a sample of stratum corneum sealing over a cylindrical dish containing water, the whole being placed in a chamber having controlled temperature and relative humidity. Sensors enable the partial pressure of water vapour to be measured at two points located at different distances from the sample. The gradient of partial pressure of water vapour between the two points, and hence the evaporation rate, may thus be determined according to Fick's law.

These studies showed that the agents of the invention reduce the evaporation rate from the skin.

It has also been possible to demonstrate the increase, as a result of the hydrating agents of the invention, in the rate of hydration of the skin by measuring its conductivity. This measurement is performed with an apparatus containing a central electrode in the form of a rod surrounded by a cylindrical electrode. The apparatus is applied to the skin. A high frequency alternating current is applied. It is found that, the greater the hydration of the skin, the larger the amount of current consumed. It is thus possible to demonstrate the increase in conductivity of the skin, and hence the increase in its rate of hydration as a result of the compositions of the invention.

Lastly, it should be noted that, in an unpublicized test carried out on 60 users with dry skin, after one month of daily application of an emulsion containing at least one salification product of a compound of formula I with a primary amine, 80% of these users noticed a hydrating activity.

These various properties of the salts of the invention enable them to be used advantageously in cosmetic or dermopharmaceutical compositions, in the form of emulsions intended, in particular, for improving the appearance of dry skins.

The compositions in the form of emulsions containing the said primary amine salts are stable, in contrast to the emulsions obtained with the urethane derivatives described hitherto.

Hence the subject of the invention is also a cosmetic or dermopharmaceutical composition which takes the form of an emulsion and which contains at least one primary amine salt or salification product with a primary amine, as defined above.

The composition of the invention contains, for example, from 1 to 10%, and especially from 2 to 5%, by weight of at least one of the said salts or salification products.

The compositions of the invention generally contain, by weight, at least 10% of oil, and most often 20 to 80%.

All oils used in the production of cosmetic compositions are suited to the production in the form of emulsions of the invention. There may be mentioned, for example, mineral oils such as liquid paraffin; vegetable oils, for example apricot kernel oils, jojoba oil; fatty esters; and silicone oils, including volatile silicone oils.

On account of the emulsifying properties of the primary amine salts of the derivatives of formula I, it is possible to produce compositions free from other emulsifying agents.

It is, however, possible to use, for the preparation of the compositions in the form of emulsions of the invention, a co-emulsifying agent. Preferably, the primary amine salts or salification products are present in the composition in the proportion of at least 10 mol %, and preferably in the proportion of at least 50 mol %, relative to the collective emulsifiers (that is to say primary amine salts+co-emulsifiers).

Among co-emulsifying agents, there may be mentioned, for example, derivatives of unsaturated or branched fatty acids or alcohols, cholesterol and α-phytanetriol. It is possible to use, in particular, oleic, linoleic, linolenic or isostearic acid, oleic alcohol, isostearyl alcohol and mono- or polyglycerolated oleates and isostearates.

To prepare the composition in emulsion form of the invention, it is possible, for example, to heat the aqueous phase containing the derivative of formula I to a sufficient temperature, for example 80° C., to facilitate its solubilization. The primary amine used for the salification may be present in the starting material or added after heating. The primary amine is added in a sufficient amount for the pH of the final product to be within the range from 6 to 7.5. Naturally, if the composition contains other acidic products (for example thickening agents of the Carbopol type), the amount of primary amine must be sufficient to neutralize both the derivatives of formula I and the other acidic products present in the composition. The oily phase is then added with vigorous agitation to create an emulsion.

If co-emulsifying agents are used, these are preferably added with the oily phase.

The compositions of the invention can also contain thickening or gelling agents for the aqueous phase, for example in a proportion of 0.5 to 10% by weight relative to the total weight of the composition. The thickening agents can consist of cellulose derivatives, acrylic polymers, alginates, gums such as xanthan, guar and carob gum and gum arabic, or alternatively polyethylene glycols.

The compositions of the invention can, in addition, contain other known hydrating or humectant agents, such as glycerol, triacetin or, more generally, other active ingredients such as agents which counteract skin ageing.

The compositions of the invention can also contain standard adjuvants such as antioxidants, perfumes, colorants, and the like.

Among antioxidants which can be used, tert-butyl hydroquinone, butylated hydroxytoluene and alpha-tocopherol and its derivatives may be mentioned.

The primary amine salts of the derivatives of formula I also have bactericidal properties which enable compositions to be produced without the addition of other preservatives. It is naturally possible, however, to use standard preservatives such as methyl, ethyl, propyl, butyl and isobutyl p-hydroxybenzoates (parabens), 2-phenoxyethanol, sorbic acid, potassium sorbate, hexamidine diisethionate, imidazolidinylurea (trade name Germall 115), or alternatively the preservatives marketed under the names Kathon and Triclosan.

When the primary amine salts or salification products of the derivatives of formula I are used as preponderant emulsifying agents, the emulsions obtained are oil-in-water type emulsions. However, with co-emulsifying agents having a suitable HLB (hydrophilic-lipophilic balance) value, it is also possible to obtain compositions in the water-in-oil form.

The compositions of the invention can be emulsions of liquid or semi-liquid consistency of the milk type, obtained by dispersion of a fatty phase in an aqueous phase or vice versa; or suspensions or emulsions of soft consistency of the cream type.

The compositions of the invention are, in particular, white emulsions constituting hydrating care creams, body milks, make-up removal products for the face, and creams containing various active agents, for example creams with slimming active agents (in particular caffeine) or anti-acne agents (for example tioxolone) or keratolytic agents (for example salicylic acid). When they are free from oils other than silicone oils, these compositions can also constitute creams for fatty skins.

The compositions of the invention can also constitute standard tinted emulsions such as make-up foundations, hydrating fluid compositions for skin care, eyeliners, and the like.

The subject of the invention is also the use of at least one salt or salification product as defined above as emulsifying or co-emulsifying agent enabling the stability of emulsions which are to contain derivatives of formula I to be improved. Naturally, the emulsions referred to here are ones in which the derivatives of formula I (in the form of primary amine salts), while playing the part of emulsifying agents, are used on account of their skin hydrating property.

The examples which follow illustrate the invention.
In these examples, the compound A represents

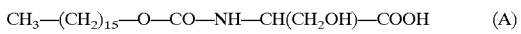

$$CH_3-(CH_2)_{15}-O-CO-NH-CH(CH_2OH)-COOH \quad (A)$$

The compound B represents 2-amino-2-hydroxy-methyl-1,3-propanediol.

EXAMPLE 1
Care Cream

| | |
|---|---|
| Compound of formula A | 5 g |
| Compound B | 1.66 g |
| Methyl para-hydroxybenzoate | 0.2 g |
| Apricot kernel oil | 38.8 g |
| Propyl para-hydroxybenzoate | 0.2 g |
| Cyclomethicone D5 | 30 g |
| Water qs | 100 g |

This care cream is intended for the treatment of dry skins.

To prepare this cream, the procedure is as follows: Compounds A and B are mixed with the aqueous phase at a temperature of 80° C. until dissolution is complete. The oily phase is poured into the aqueous phase with vigorous stirring, still at a temperature of 80° C., in order to obtain an emulsion.

The compositions of the following examples were prepared in a similar manner.

EXAMPLE 2
Care Cream

| | |
|---|---|
| Compound A | 2.5 g |
| Compound B | 1.44 g |
| Apricot kernel oil | 19.8 g |
| Jojoba oil | 5 g |
| Cyclomethicone D5 | 5 g |
| Silicone gum sold under the name Q$_2$1401 by the company Dow Corning | 5 g |
| Propyl para-hydroxybenzoate | 0.2 g |
| Carbopol 980 (Goodrich) | 0.75 g |
| Methyl para-hydroxybenzoate | 0.2 g |
| Water qs | 100 g |

This care cream, which is both light and hydrating, is especially well suited to dry and dehydrated skins.

EXAMPLE 3
Body Milk

| | |
|---|---|
| Compound A | 2.5 g |
| Aminomethylpropanol (AMP) | 1.3 g |
| Isostearic acid | 1.94 g |
| Jojoba oil | 20 g |
| Cyclomethicone D5 | 15 g |
| Carbopol 980 | 0.5 g |
| Xanthan gum | 0.2 g |
| Methyl para-hydroxybenzoate | 0.2 g |
| Propyl para-hydroxybenzoate | 0.2 g |
| Water qs | 100 g |

This body milk, which is of very light structure, is suitable for normal and dry skins, which rapidly regain a high level of hydration.

EXAMPLE 4
Make-up Foundation

| | |
|---|---|
| Compound A | 2.5 g |
| Compound B | 1.44 g |
| Carbopol 980 | 0.75 g |
| Methyl para-hydroxybenzoate | 0.2 g |
| Apricot kernel oil | 25 g |
| Cyclomethicone D5 | 9.8 g |
| Propyl para-hydroxybenzoate | 0.2 g |
| Black iron oxide | 0.11 g |
| Red iron oxide | 0.39 g |
| Yellow iron oxide | 0.6 g |
| Titanium dioxide | 2.9 g |
| Water qs | 100 g |

This make-up foundation, which is of very light texture, has a hydrating effect like a care cream. It is especially suitable for dry and dehydrated skins.

EXAMPLE 5
Cream for Skin Which Tends to be Greasy

| | |
|---|---|
| Compound A | 2.5 g |
| AMP | 1.5 g |
| Glycerol | 3 g |
| Oleic acid | 1.94 g |
| Cyclomethicone D5 | 35 g |
| Carbopol 980 | 0.75 g |
| Methyl para-hydroxybenzoate | 0.2 g |
| Propyl para-hydroxybenzoate | 0.1 g |
| Water qs | 100 g |

EXAMPLE 6
Fluid Cream

| | |
|---|---|
| Compound A | 1.8 g |
| AMP | 1.26 g |
| Apricot kernel oil | 15 g |
| Volatile silicone oil (Cyclomethicone D5) | 10 g |

-continued

| Isostearic acid | 1.2 g |
| Carbopol 980 | 0.75 g |
| Preservatives | 0.3 g |
| Water gs | 100 g |

This cream is pliant and very light when applied. It is especially suitable for normal and greasy skins.

EXAMPLE 7
Emollient Care Cream

| Compound A | 2.5 g |
| Lysine | 2.73 g |
| Oleic acid | 1.94 g |
| Apricot kernel oil | 19.7 g |
| Cyclomethicone D5 | 15 g |
| Propylene glycol | 5 g |
| Preservatives | 0.3 g |
| Water qs | 100 g |

This cream, which is especially mild, is suitable for dry and sensitive skins, which it hydrates.

EXAMPLE 8
Cream for Dry Skins

| N-Dodecyloxycarbonylserine | 5 g |
| Compound B | 1.98 g |
| Preservatives (parabens) | 0.3 g |
| Apricot kernel oil | 70 g |
| Water qs | 100 g |

This cream, which has a hydrating effect, is intended for dry skins.

We claim:

1. A primary amine salt of a derivative of formula (I):

R'O—CO—NH—CH(R)—COOH    (I)

in which:

R represents —CH$_2$OH or —CHOH—CH$_3$, and R' represents an optionally unsaturated alkyl group having at least 10 carbon atoms, or an at least partial salification product of the derivative of formula (I) with a primary amine, the degree of salification of which is sufficient to obtains at a concentration of at least 1%, a pH above 6 and below 7.5 in aqueous solution; said primary amine corresponding to the formula (II):

H$_2$N—CR$_1$(R$_2$)(R$_3$)    (II)

wherein R$_1$ represents —CH$_2$OH, and R$_2$ and R$_1$ independently represent an optionally hydroxylated lower alkyl, or said primary amine is an amino acid containing at least two amino groups.

2. A salt or salification product according to claim 1 wherein R' contains from 10 to 20 carbon atoms.

3. A salt or salification product according to claim 2 wherein R' contains from 14 to 18 carbon atoms.

4. A salt or salification product according to claim 3 wherein R' contains 16 carbon atoms.

5. A salt or salification product according to claim 1 wherein R$_2$ represents —CH$_3$ or —CH$_2$OH, and R$_3$ represents —CH$_3$, —C$_2$H$_5$ or —CH$_2$OH.

6. A salt or salification product according to claim 5 wherein the primary amine is chosen from 2-amino-2-methyl-1,3-propanediol, 2-amino-2-methyl-1-propanol and 2-amino-2-hydroxymethyl-1,3-propanediol.

7. A salt or salification product according to claim 1 wherein the primary amine is chosen from lysine and arginine.

8. Cosmetic or dermopharmaceutical composition, in the form of an emulsion, comprising at least one salt or salification product of claim 1 as emulsifying agent.

9. Composition according to claim 8 wherein said at least one salt or salification product is present in an amount of from 1 to 10% by weight.

10. Composition according to claim 9 wherein said amount is 2 to 5%, by weight.

11. Composition according to claim 9 wherein said salt or salification product is the sole emulsifying agent.

12. Composition according to claim 10 wherein said salt or salification product is the sole emulsifying agent.

13. Composition according to claim 9 further comprising a co-emulsifying agent.

14. Composition according to claim 10 further comprising a co-emulsifying agent.

15. Composition according to claim 13 wherein said salt or salification product is present in the proportion of at least 10 mol %, relative to the emulsifying agents.

16. Composition according to claim 14 wherein said salt or salification product is present in the proportion of at least 10 mol %, relative to the emulsifying agents.

17. Composition according to claim 13 wherein said co-emulsifying agent is chosen from oleic acid, linoleic acid, linolenic acid, isostearic acid, oleyl alcohol, isostearyl alcohol, monoglycerolated oleates, polyglycerolated oleates, monoglycerolated isostearates, polyglycerolated isostearates, cholesterol and α-phytanetriol.

18. Composition according to claim 15 wherein said co-emulsifying agent is chosen from oleic acid, linoleic acid, linolenic acid, isostearic acid, oleyl alcohol, isostearyl alcohol, monoglycerolated oleates, polyglycerolates, monoglycerolated isostearates, polyglycerolated isostearates, cholesterol and α-phytanetriol.

19. Composition according to claim 8, further comprising by weight, at least 10% of oil.

20. A process for improving the stability of a cosmetic composition in emulsion form, comprising adding, as an emulsifying or co-emulsifying agent, at least one salt or salification product according to claim 1 to said composition.

21. The process according to claim 20 wherein the salts or salification products are added as the sole emulsifying agent.

22. The process according to claim 20 wherein said salt or salification product is added with at least one co-emulsifying agent.

23. The process according to claim 20 wherein said salt or salification product is present in the proportion of at least 10 mol %, relative to the collective emulsifying agents.

24. The process according to claim 23 wherein said proportion is at least 50 mol %.

25. A salt or salification product of claim 1 wherein said primary amine corresponds to the formula (II).

* * * * *